United States Patent [19]
Rice

[11] Patent Number: 4,737,467
[45] Date of Patent: Apr. 12, 1988

[54] VAPOR STRIPPING CELL AND A METHOD FOR SEPARATING ORGANIC VAPORS FROM AN ORGANIC SUBSTANCE

[76] Inventor: Richard C. Rice, 568 Sunset Dr., Pittsburgh, Pa. 15237

[21] Appl. No.: 11,676

[22] Filed: Feb. 6, 1987

[51] Int. Cl.$^4$ .................. G01N 1/18; B01L 11/06; B01L 3/00
[52] U.S. Cl. .................. 436/177; 422/101; 422/99; 55/47
[58] Field of Search ............ 422/68, 69, 224, 99, 422/101, 209, 224, 270; 55/182, 159, 47; 366/219, 237, 167, 173, 174; 210/512.1, 787; 159/9.2, 11.2, 900, 49; 436/177

[56] References Cited

U.S. PATENT DOCUMENTS 2,381,210  8/1945  Cotton .................. 422/101
3,098,718  7/1963  Ferrari .................. 422/99
4,567,748  2/1986  Klass et al. .................. 422/99

Primary Examiner—David L. Lacey
Assistant Examiner—Lyle Alfandary Alexander
Attorney, Agent, or Firm—William J. Ruano

[57] ABSTRACT

A vapor stripping cell for the transfer of volatile organic substances from either an aqueous phase of a solids sample dispersed in an aqueous phase to a suitable vapor trapping medium for subsequent gas chromatographic analysis. It comprises a bottle-like cell into which extends a tube terminating adjacent the perimetrical portion of the bottom of said cell for introducing organic substance to be tested. A drive is provided for oscillating the bottom of said cell while maintaining the top substantially stationary to spread said substances substantially uniformly on the inner surface of said cell.

5 Claims, 1 Drawing Sheet

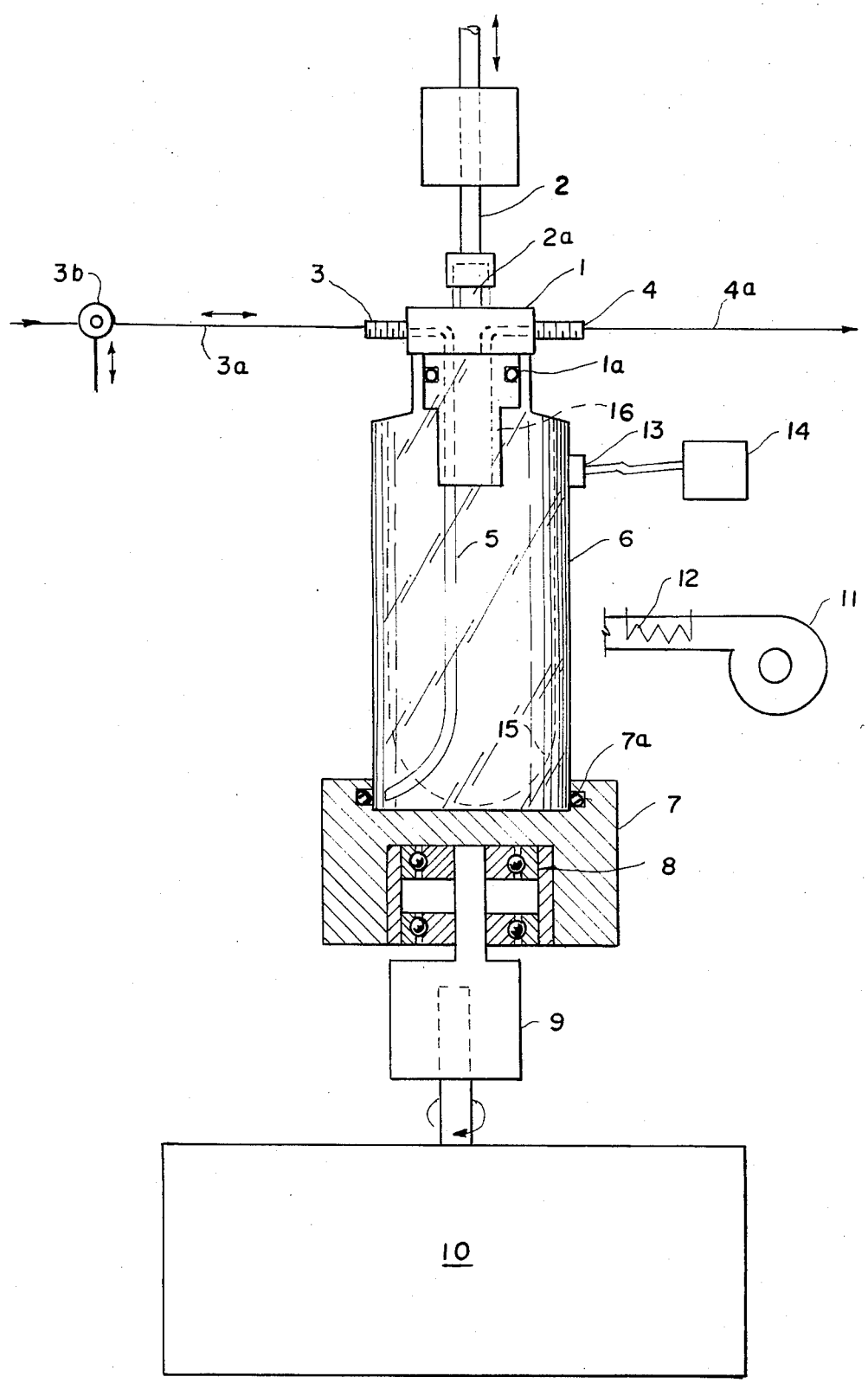

4,737,467

VAPOR STRIPPING CELL AND A METHOD FOR SEPARATING ORGANIC VAPORS FROM AN ORGANIC SUBSTANCE

This invention relates to a vapor stripping cell for the analytical transfer of volatile organic substances from either an aqueous phase or a solids sample dispersed in an aqueous phase to a suitable vapor trapping medium for subsequent gas chromatographic analysis.

BACKGROUND OF THE INVENTION

The present captive or fixed type cells are of complex construction, difficult to clean and costly in construction. The advantages of the present invention recited hereinafter, will show a more detailed comparison.

SUMMARY OF THE INVENTION

The unit is based on the use of a mechanically agitated cell in which high speed oscilatory agitation is used to (1) produce a turbulent aqueous film or layer of maximum area over the inside surface of the purge cell to facilitate rapid liquid/gas transfer characteristics (2) to rapidly disperse suspended solids such as soils in the cell's aqueous phase and (3) mechanically induce agitation of the cell's contained gas volume.

DETAILED DESCRIPTION OF THE DRAWING

The single FIG. of the drawing shows the vapor stripping cell of the present invention with parts shown schematically.

DETAILED DESCRIPTION OF A PREFERRED EMBODIMENT

The present invention is based on four components (1) expendable 40 cubic centimeter (or larger) glass vials or bottles for the purge cell (2) a specially designed stainless steel cell entry fitting to provide the necessary connection routing and sealing of the purge gas to the glass cell (3) a mechanical drive and mounting system to induce non rotating oscilatory agitation at the bottom of the cell and clamped zero motion at the top of the cell and (4) a heating system to rapidly heat and control the cell purging temperatures for enhanced insitu vapor purging. The advantages of such a system over the current captive or fixed type cells would be:

the ability to analyse either liquids or solids (aqueous dispersions);

the use of disposable vials or bottles to facilitate cleaning;

the ability to either prefill the cell (in the field or at the point of analysis) or to indirectly syringe inject aqueous samples into the cell by means of a suitable multiport valve;

the ability to use preweighed and capped cells (vials) for solids analysis in which calculations would be based on post analytical weighing (after controlled oven drying).

This would both minimize the volitile losses associated with the normal pre-analyses sample manipulations (sample weighing, transfers and mechanical solids dispersions conducted under atmospheric contact) and greatly speed up the total analytical process; and compatability with existing automated purge systems.

SYSTEM OPERATION

The sample to be stripped of volitiles can be entered into the purge cell in two ways:

(A) By direct entry into an open cell 6 with subsequent capping and sealing of the cell with the entry fitting 1;

(B) By direct syringe injection into the carrier gas inlet line by means of a suitable multiport valve 3b located on the purge gas inlet line 3a.

The cell 6 assembled with fitting 1 is set into its oscilatory base 7,7a and secured to it's top pivot assembly 2,2a.

The connective plastic purge gas line 3a from the regulated gas source and the discharge line 4a to the trap tube, (not shown) if not already connected should be connected to the swagelock fittings 3,4 located on the entry fitting.

The electric motor 10 rotation is converted into a 3/16 inch non rotative oscillatory action by the crank/bearing assembly (8,9) and is coupled to the cell by a plastic cell base (7) and rubber coupling (7a).

The oscilatory agitation imparted to the extraction cell results in the establishment of a turbulent film of the aqueous or aqueous dispersed solid sample over the interior surface of the cell as shown by the dotted lines.

A stainless steel interior cell tube 5 extending from the entry fitting to the bottom of the cell 6 serves a multiple function; to convey the carrier gas to the bottom of the cell and into the liquid for rapid subsurface dispersion of the gas into aqueous sample, as a cell entry and discharge point for remote sample addition and removal and, as a stirring blade, to both achieve rapid dispersion of solids into the aqueous phase and to provide agitation to the cells contained gas phase.

The carrier gas in the cell interior exits the cell through a splash guard chamber 16 machined into the cap to minimize possible sample carryover to the exiting as stream.

A heating system including air blowers 11 and electrical heating element 12 rapidly heats and controls the purging temperature of cell 6 for enhanced insitu vapor purging. The heat is controlled by temperature sensor 13 and temperature controller 14.

Thus it will be seen that I have provided a novel vapor stripping cell for the alalylical transfer of votatile organic substances from either an acqueous phase or a solids sample dispersed in an acqueous phase to a suitable vapor trapping medium for subsequent gas chromatic analysis. Also I have provided a cell system which is simple in construction and operation, involving a minimum number of inexpensive readily available parts which system operates rapidly with great accuracy and reliability.

While I have illustrated and described a single specific embodiment of my invention, it will be understood that this is by way of illustration only and that various changes and modifications may be contemplated in my invention within the scope of the following claims.

I claim:

1. Apparatus comprising a cell in the form of a cylindrical bottle having a bottom and top for containing aqueous organic substances and a stationarily mounted tube curved outwardly at the bottom of the bottle and terminating adjacent to the perimetrical portion of the bottom of said cell for introducing organic substances to be tested and a means for oscillating the bottom of said cell at high speed along a unidirectional, non-rotative, orbital oscillatory path while maintaining the top substantially stationary so as to spread substances substantially uniformly over a maximum area on the inner surface of said cell to facilitate rapid liquid/gas transfer characteristics.

2. Apparatus as recited in claim 1 wherein said oscillation means comprises an electrical motor driving crank means, including anti-friction elements.

3. Apparatus as recited in claim 2 further including means for controlling the temperature of said cell.

4. Apparatus as recited in claim 1 wherein said cell is open at said top and said apparatus further includes a multi-port entry fitting connected to said top of cell for introduction and exiting of said organic substances.

5. A method for separating organic vapors from an organic substance in a liquid comprising introducing liquid containing said substance into a cylindrical cell, oscillatting the bottom of said cell at high speed along a unidirectional non rotating orbital path while keeping its top relatively stationary, said high speed being sufficient to uniformly disperse said liquid on the interior surface of said cell over a maximum area so as to separate said organic substances from the vapors, and simultaneously conducting said organic vapors away from said cell by flowing a carrier gas through said cell.

* * * * *